United States Patent
Da Silva et al.

(10) Patent No.: US 7,494,492 B2
(45) Date of Patent: Feb. 24, 2009

(54) SKIN TREATMENT DEVICE

(75) Inventors: Luiz B. Da Silva, Danville, CA (US);
George Choi, Redwood City, CA (US)

(73) Assignee: Therative, Inc., Livermore, CA (US)

( * ) Notice: Subject to any disclaimer, the term of this patent is extended or adjusted under 35 U.S.C. 154(b) by 173 days.

(21) Appl. No.: 11/216,595

(22) Filed: Aug. 30, 2005

(65) Prior Publication Data

US 2006/0129214 A1    Jun. 15, 2006

Related U.S. Application Data

(60) Provisional application No. 60/634,904, filed on Dec. 10, 2004.

(51) Int. Cl.
*A61B 18/08* (2006.01)

(52) U.S. Cl. .......................... 606/99; 606/98

(58) Field of Classification Search .............. 606/9, 606/13, 20, 27–31, 41–51; 607/88, 96–102, 607/108
See application file for complete search history.

(56) References Cited

U.S. PATENT DOCUMENTS

| | | | |
|---|---|---|---|
| 4,449,528 A * | 5/1984 | Auth et al. ........................ | 606/31 |
| 4,860,744 A * | 8/1989 | Johnson et al. .................. | 606/31 |
| 5,593,406 A | 1/1997 | Eggers et al. | |
| 5,830,211 A * | 11/1998 | Santana et al. .................. | 606/27 |
| 6,066,153 A | 5/2000 | Lev | |
| 6,162,211 A * | 12/2000 | Tankovich et al. ............... | 606/9 |
| 6,176,856 B1 | 1/2001 | Jandak et al. | |
| 6,228,078 B1 * | 5/2001 | Eggers et al. .................... | 606/32 |
| 6,235,027 B1 * | 5/2001 | Herzon ........................... | 606/51 |
| 6,245,093 B1 | 6/2001 | Li et al. | |
| 6,635,075 B2 * | 10/2003 | Li et al. ........................... | 607/96 |
| 6,740,085 B2 * | 5/2004 | Hareyama et al. ............... | 606/51 |
| 7,137,979 B2 * | 11/2006 | Conrad et al. ................... | 606/31 |

(Continued)

FOREIGN PATENT DOCUMENTS

WO    WO 89/04137    5/1989

(Continued)

OTHER PUBLICATIONS

Bruce, et al. Significant efficacy and safety of low level intermittent heat in patients with mild to moderate acne. (No publication information).

(Continued)

*Primary Examiner*—Roy D Gibson
(74) *Attorney, Agent, or Firm*—Squire, Sanders & Dempsey, L.L.P.

(57) ABSTRACT

A compact hand held device is provided that can be safely used by those suffering from acne, blemished skin or fine wrinkles. The hand held device includes an on/off switch and a button that pulses the device when it is placed on the target site. A battery within the device powers a circuit board and drives a short pulse of current through a heating element, which heats up to approximately 300° C. in less than 0.1 sec. Thermal conduction transfers the heat to the skin and causes a biological response that accelerates acne clearing, treats blemished skin or fine wrinkles. The total heat transferred is low enough to prevent burns. Application of acne treatment creams and gels further accelerates treatment

17 Claims, 6 Drawing Sheets

U.S. PATENT DOCUMENTS

| 7,170,034 | B2 * | 1/2007 | Shalev et al. ............... 219/223 |
| 2004/0127962 | A1 | 7/2004 | Li et al. |
| 2005/0203596 | A1 | 9/2005 | Li et al. |
| 2005/0288748 | A1 | 12/2005 | Li et al. |

FOREIGN PATENT DOCUMENTS

WO      WO 96/35469      11/1996

OTHER PUBLICATIONS

Elman, et al. The role of pulsed light and heat energy (LHE) in acne clearance. J. of Cosmet. and Laser Ther. 2004; 6(2):91-95.

Gold, et al. The use of a novel intense pulsed light and heat source and ALA-PDT in the treatment . . . J. Drugs Dermatol. 2004; 3(6):S15-19.

Henriques, F. C. Studies of thermal injury. Archives of Pathology. 1947; 43(5):489-502.

Paithankar, et al. Acne threatment with a 1,450 nm wavelength laser and cryogen spray cooling. Lasers in Surgery and Medicine. 2002; 31:106-114.

Ruiz-Esparza, et al. Nonablative radiofrequency for active acne vulgaris, Dermatol Surg. 2003; 29(4):333-9.

Tye, et al. Acne treated wtih compress and a corticosteroid cream. Archives of Dermatology. 1964; 89:201-203.

European Search Report for PCT/US2005044547, mailed Apr. 23, 2008, 7 pgs.

* cited by examiner

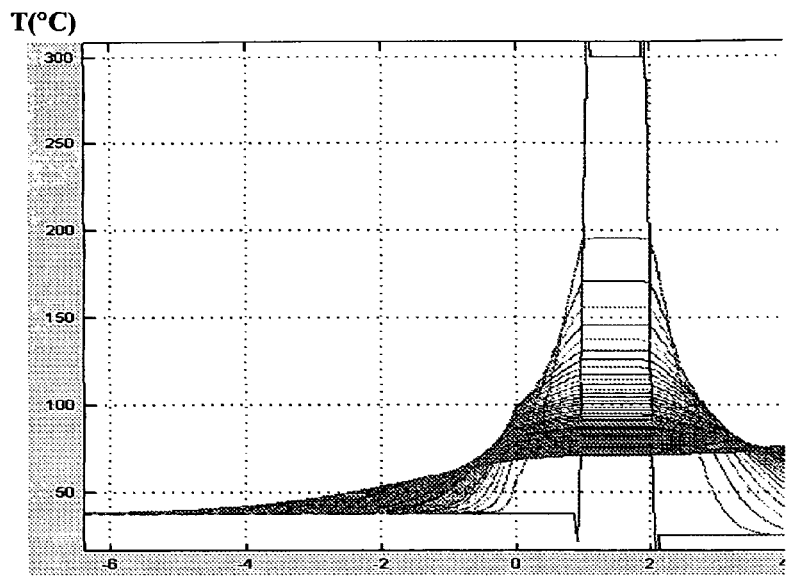
Figure 7 Temperature profile along the central axis of the treatment device in contact with skin. The skin surface is at 0, x-axis is in hundreds of μm's. Time between curves is 20 ms.
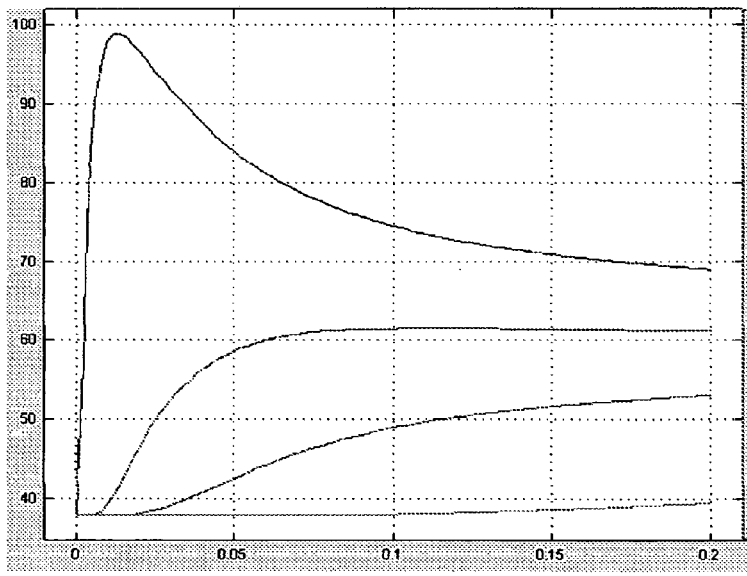
Figure 8 Temperature history (0 to 0.2 secs) at skin surface (blue), and 100 μm (green) ,200 μm (red), 500 μm (teal) into tissue.

SKIN TREATMENT DEVICE

This application claims priority to U.S. Provisional Patent Application Ser. No. 60/634,904, titled "Skin Treatment Device," filed Dec. 10, 2004, incorporated herein by reference.

BACKGROUND OF THE INVENTION

1. Field of the Invention

The present invention relates to the fields of skin care and more particularly, it relates to a device and method for treating acne, removing fine wrinkles and clearing skin.

2. Description of Related Art

Acne affects more than 90% of all adolescents, nearly 50% of all adult women and 25% of all adults. One of the main causes of acne is improper drainage of the hair follicle caused by a plug of dead cells or dirt that trap oil and bacteria. The hair follicle opening is approximately 50 μm to about 100 μm in diameter. The opening of any other pore on the skin is substantially smaller. In particular, the opening of a sweat pore is less than about 30 μm in diameter.

There are a variety of ways to treat acne. Benzoyl Peroxide is one of the most commonly used ingredients in over-the-counter treatments, and it can be very effective in treating mild cases of non-inflammatory acne. It is safe for children as well as adults, and may be combined with other topical or oral treatments. For patients who suffer from moderate to severe acne, doctors may prescribe a combination of topical remedies and oral antibiotics. The most common oral medications used to treat acne are tetracycline, minocycline, doxycycline and erythromycin.

Alternatives to medication include UV light radiation, laser treatment, or abrasion. Most of these systems are large and in most cases require professional treatment U.S. Pat. No. 6,635,075 by Li et al. describes a heating device that can also be used to treat acne. The device described in therein uses a heater and temperature sensor to maintain a constant temperature surface that can be applied to skin. In order to prevent burns during the long application time (minutes), the maximum temperature allowed is 62° C. The long treatment time makes this device impractical for normal acne treatment A need exists for a compact device that can be used effectively and quickly to treat acne. The present invention fulfills this need, and further provides related advantages.

SUMMARY OF THE INVENTION

It is an object of the present invention is to provide a device and method for treating acne, removing fine wrinkles and clearing skin.

Another object of the present invention is to provide a hand held device that can be safely used to heat a thin layer of tissue without causing a burn.

These and other objects will be apparent to those skilled in the art based on the teachings herein.

The present invention is a compact hand held device that can be safely used by adolescents and adults suffering from acne, blemished skin or fine wrinkles. In one embodiment, the present invention comprises a hand held device with an on/off switch and a button that pulses the device when it is placed on the target site. A battery within the device powers a circuit board and drives a short pulse of current through a thin film resistor. The thin film resistor heats up to approximately 300° C. in less than 0.1 sec. Thermal conduction transfers the heat to the skin and causes a biological response that accelerates acne clearing. The total heat transferred is low enough to prevent burns, typically less than 50 J/cm$^2$ and for most applications less than 5 J/cm$^2$.

In another embodiment, of the present invention Ultra-bright LEDs are integrated into the device to provide illumination in the blue or red spectral range to improve treatment.

The present invention can also be combined with acne treatment creams and gels to further accelerate treatment For example, creams or gels containing benzoyl peroxide could be applied before or after applying the device.

Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

FIG. 7 shows a temperature profile along the central axis of the treatment device in contact with skin.

FIG. 8 shows a temperature history at the skin surface.

DETAILED DESCRIPTION OF THE INVENTION

Figure 1:
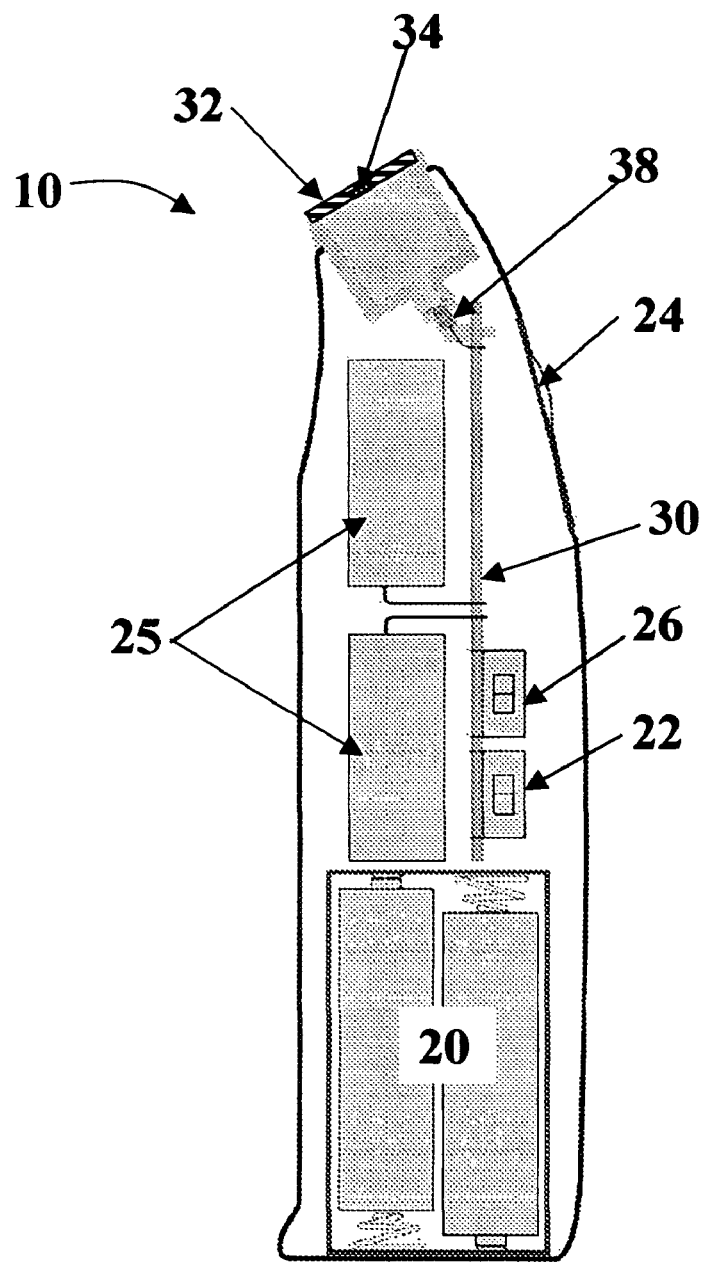
FIG. 1 shows a sectional view taken through the handheld acne treatment device that uses a thin film resistor to deliver energy into the skin.

FIG. 1 shows a cross-sectional view of the hand held treatment device 10. The device consists of a battery 20 that powers a circuit board 30. The circuit board 30 is activated with power switch 22 to charge a capacitor 25 that stores enough energy to heat a heating element (e.g., a thin resistive heater) 32 to the necessary temperature (100-400° C.). The capacitor 25 is discharged through the resistor 32 when button 24 is pushed. The circuit will then recharge the capacitor and be ready to fire again within a few seconds. In order to reduce the risk of accidental burns, the heating element is allowed to cool before another heating pulse can be fired. In one embodiment, a temperature sensor (e.g., thermocouple) 34 monitors the temperature of the heating element and prevents a second heating pulse until the temperature drops below an acceptable temperature (e.g., 40° C.). The thin resistive heater is typically made of metal (e.g., Nichrome (Nickel and Chromium alloy), tungsten, aluminum, copper, gold, steel) and is typically less than 200 μm thick. Suitable thin film resistors can also be found at Minco Products, Inc. (http://www.minco.com/) (e.g., Thermofoil™ heaters). Other suitable thin film resistors are available from Kyocera, Inc.

In one embodiment the user can select different power levels. For example, as shown in FIG. 1 a high and low power setting can be selected using button 26. An optional LED 38 can also be integrated into the device to provide illumination and aid in treatment. For example blue and red light has been shown to treat acne.

Figure 2:
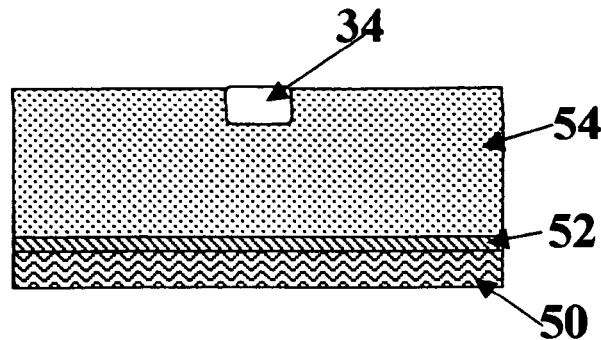
FIG. 2 shows a sectional view taken through one embodiment of the heating element, which includes a thick backing layer.
Figure 3:
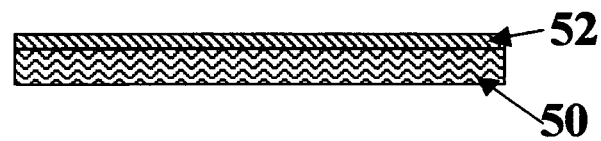
FIG. 3 shows a sectional view taken through another embodiment of the heating element.
Figure 4:
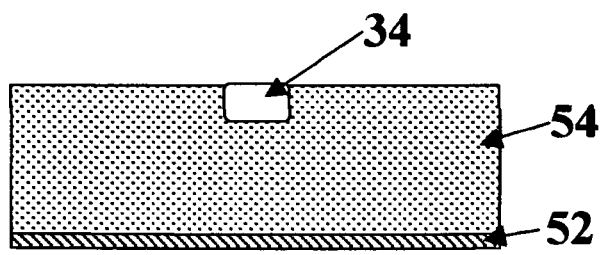
FIG. 4 shows a sectional view taken through another embodiment of the heating element.

FIGS. 2, 3 and 4 show exemplary embodiments that may be substituted for the heating element 32. A thick backing layer 54, shown in FIGS. 2 and 4, can be used to add strength to the heating element and also conduct heat away from the thin resistive heater 52. In one embodiment, a thin protective layer 50 covers the resistive heater. In the preferred embodiment, the protective layer 50 is an electrical insulator and has good thermal conductivity. This protective layer 50 reduces the risk of shock to the user and can act to improve temperature uniformity across the surface of the heating element Alternatively the thin resistive heater 52 can be chemically treated (e.g., anodized) to provide a very thin insulating layer to prevent electrical shock to the user. For most applications the thin resistive heater 52 and optional protective layer 50 are less than 500 μm thick to limit the total energy required to heat the material to the necessary peak temperature. This also limits the maximum energy that can be transferred into the tissue thereby reducing the risk of burns. A temperature sensor 34, shown in FIGS. 2 and 4, can be integrated into the backing layer 54 to monitor temperature. For most applications the surface area of the heating element is approximately 1 $cm^2$.

The heating element in the present invention will quickly cool by thermal conduction into tissue (and into the backing layer, if present, as well). The maximum energy that can be transferred to the skin is limited to the total thermal energy generated within the heating element. Total thermal energy is determined by the peak temperature and the thickness of the heated layer. For example, for a 100 μm thick copper element heated to 300° C., the available energy to transfer to tissue that is at 30° C. is approximately 9.2 $J/cm^2$. The relaxation time is approximately 8.65 μsec. Table 1 and Table 2 below summarize the relaxation time and required energy for different materials and thicknesses.

TABLE 1

Relaxation time for different materials of specified thickness (assuming planar)

| Material | Relaxation Time [μseconds] (100 μm thick) | Relaxation Time [μseconds] (200 μm thick) |
| --- | --- | --- |
| aluminum | 10.45 | 41.8 |
| copper | 8.65 | 34.6 |
| Glass | 1220.75 | 4883 |
| Graphite | 12.675 | 50.7 |
| Water | 7237.2 | 28948.8 |

TABLE 2

Energy per $cm^2$ required to heat material of specified thickness by 270° C.

| Material | Energy [Joules/$cm^2$] (100 μm thick) | Energy [Joules/$cm^2$] (200 μm thick) |
| --- | --- | --- |
| aluminum | 6.78 | 13.56 |
| copper | 9.2 | 18.4 |
| glass | 5.67 | 11.34 |
| graphite | 3.45 | 6.9 |
| water | 11.3 | 22.6 |

Making appropriate selection of materials and thickness allows one to control the peak tissue temperature and duration.

Figure 5:
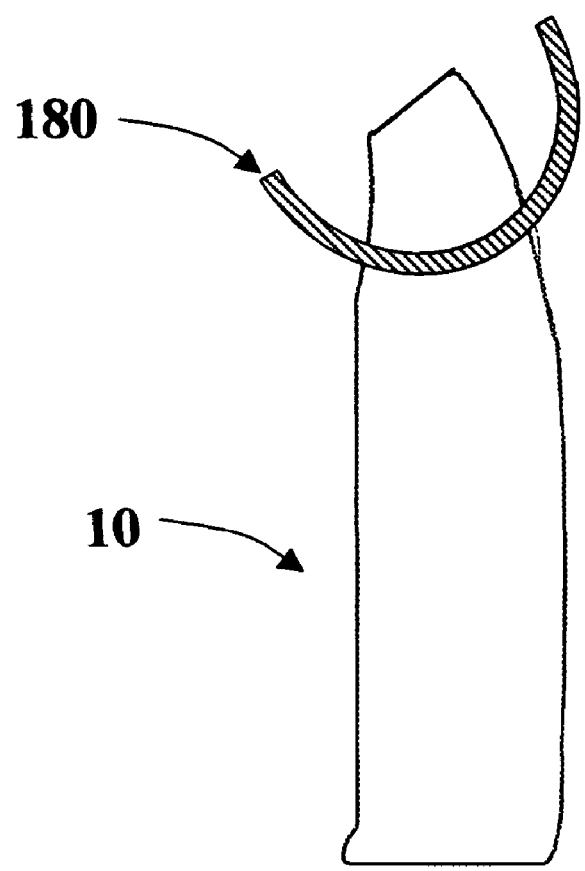
FIG. 5 shows another embodiment of the handheld acne treatment device that integrates a protective shield.

FIG. 5 shows another embodiment of the handheld acne treatment device that integrates a protective shield 180 to prevent the user from positioning the device on the eye.

Figure 6:
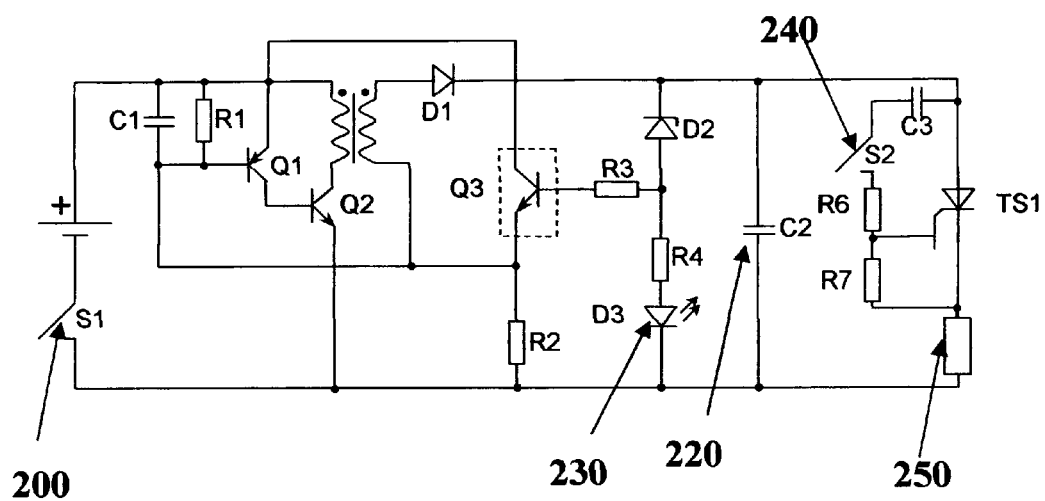
FIG. 6 shows one possible circuit diagram for pulsing the thin film resistor.

FIG. 6 shows one possible circuit to pulse the thin resistive heater to the desired peak temperature. A switch 200 (S1) is turned on to activate the device and charge the capacitor 220 (C2). When the capacitor is fully charged, a lamp 230 LED (D3) turns on and the device is ready to fire. When the fire switch 240 (S2) is activated, it turns on the thyristor (TS1) and discharges the capacitor 220 through the thin resistive heater 250. In the preferred embodiment the discharge through the thin resistive heater has a time constant of less than 10 ms. The capacitor 220 begins to charge again after firing and after several seconds (depending on battery and resistance) is fully charged. This circuit releases a maximum energy per pulse of ½ $CV^2$ where C is the capacitor capacitance and V is the final voltage across the capacitor. By selecting appropriate values of C and V, the released energy can be kept below the threshold for tissue burns.

FIG. 7 shows the calculated temperature profile along the central axis of the treatment device. The thin metal heater is located between 1-2 on the x-axis and quickly cools after heating by thermal conduction into the skin. FIG. 8 shows the temperature history at the skin surface, 0.2 mm below surface and 0.5 mm below the skin surface. The high peak temperatures exist for less than 0.1 seconds.

The short time duration of the high peak temperature is critical to preventing skin burns. Henriques (F. C. Henriques, "Studies of Thermal Injury: The Predictability and the Significance of Thermally Induced Rate Processes Leading to Irreversible Epidermal Injury", Archives of Pathology, 43, 5 May 1947, Pages 489-502) published a theory on skin burns based on a form of the Arrhenius equation for heat induced irreversible chemical reaction. Although numerous other studies have investigated the burn process, the conclusions are similar. A skin burn occurs as a result of thermally induced changes in protein structure that have an activation energy of about 600 MJ/kg-mol. For skin the Henriques Integral equation can be written as:

$$\omega = \int_0^t e^{226.78 - \frac{75000}{T}} dt$$

where T is the temperature in Kelvin at depth x and is a function of time, and ω is a function of burn injury. Integration is carried out over the time the basal layer temperature is greater then or equal to 44° C. Second degree burns occur when ω=1. First degree burns occur for values of ω=0.53. Third degree burns occur at a critical value of ω=1 at the base of the dermis. For the present device and procedure, ω<0.4 for depths greater than 100 μm below skin surface. For this reason the risk of burn is very low.

Figure 9:
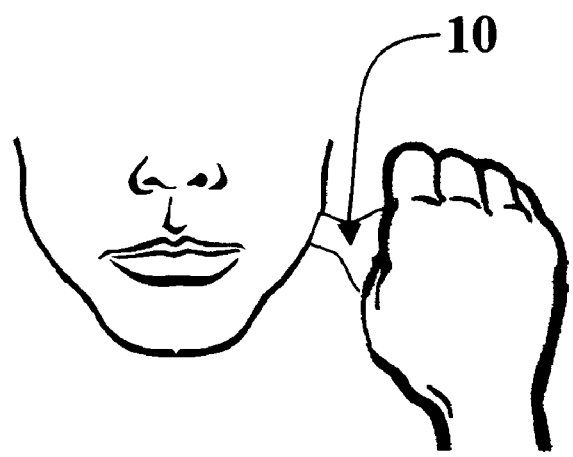
FIG. 9 shows how the treatment device might be used to treat a blemish on the face.

FIG. 9 shows how the present invention would be used to treat a blemish on the face. The device 10 is activated and then placed in contact with the skin. When the device 10 is in good contact and fully charged, the fire button is pressed to deliver energy to the heating element, which then transfers its energy to the skin. The thermal impulse to the skin acts to open pores and accelerate clearing of the blemish. In some cases, multiple treatments in one session may be necessary to effectively treat the blemish. In this case the minimum time between treatments is controlled by the circuit, which prevents misuse and possible burns. It may also be necessary to perform multiple treatments through the course of a day, or week to treat some blemishes.

The present invention can also be combined with topical gels or creams to improve treatment of acne. For example, topical gel with benzoyl peroxide can be applied after treatment with the device. For optimum results the area to be treated is first washed with mild soap or cleanser. After washing the area to be treated, the device is applied a minimum of one time and then a topical acne gel is applied. This process would usually be repeated twice a day.

The above descriptions and illustrations are only by way of example and are not to be taken as limiting the invention in any manner. One skilled in the art can substitute known equivalents for the structures and means described. The full scope and definition of the invention, therefore, is set forth in the following claims.

We claim:

1. An apparatus comprising:
a housing;
a heating element attached to said housing, wherein said heating element comprises a backing layer to add strength and to conduct heat;
means for heating said heating element to a peak temperature for a time duration of less than 1 second; and
means for controlling said peak temperature over said time duration such that said peak temperature over said time duration is at least 70° C. and will not burn human skin.

2. An apparatus comprising:
a housing;
a heating element attached to said housing, wherein said heating element includes an electrically insulating protective layer for placement directly onto skin, wherein said heating element has a surface area of about 1 cm$^2$;
means for heating said heating element to a peak temperature for a time duration of less than 1 second; and
means for controlling said peak temperature over said time duration such that said peak temperature over said time duration is at least 70° C. and will not burn human skin.

3. An apparatus comprising:
a housing;
a heating element attached to said housing, wherein said heating element includes a high thermal conductivity electrical insulator layer for placement directly onto skin to improve temperature uniformity;
means for heating said heating element to a peak temperature for a time duration of less than 1 second; and
means for controlling said peak temperature over said time duration such that said peak temperature over said time duration is at least 70° C. and will not burn human skin.

4. An apparatus comprising:
a housing;
a heating element attached to said housing, wherein said heating element comprises a resistive heater;
means for heating said heating element to a peak temperature for a time duration of less than 1 second; and
means for controlling said peak temperature over said time duration such that said peak temperature over said time duration is at least 70° C. and will not burn human skin, wherein said means for controlling said peak temperature over said time duration comprises a control circuit and a temperature sensor, and wherein said control circuit monitors said temperature sensor and prevents said heating element from heating to a temperature that would burn human skin for a given duration of time.

5. An apparatus comprising:
a housing;
a heating element attached to said housing;
means for heating said heating element to a peak temperature for a time duration of less than 1 second, wherein said means for heating said heating element comprises an electrical circuit configured to charge a capacitor that stores enough energy to heat said heating element; and
means for controlling said peak temperature over said time duration such that said peak temperature over said time duration is at least 70° C. and will not burn human skin;
a temperature sensor that comprises a thermocouple, wherein the temperature sensor is used by the controlling means to control the peak temperature of the heating element.

6. An apparatus comprising:
a housing;
a battery powered light emitting diode fixedly attached to said housing to provide illumination;
a heating element attached to said housing;
means for heating said heating element to a peak temperature for a time duration of less than 1 second; and
means for controlling said peak temperature over said time duration such that said peak temperature over said time duration is at least 70° C. and will not burn human skin.

7. An apparatus comprising:
a housing;
a heating element attached to said housing, wherein said heating element comprises a resistive heater;
means for heating said heating element to a peak temperature for a time duration of less than 1 second;
means for controlling said peak temperature over said time duration such that said peak temperature over said time duration is at least 70° C. and will not burn human skin; and
means for preventing said heating element from being heated again until said heating element has cooled to at least 50° C.

8. A method for treating skin, comprising:
providing a treatment device that includes a housing; a heating element attached to said housing; means for heating said heating element to a peak temperature for a time duration of less than 1 second; and means for controlling said peak temperature over said time duration such that said peak temperature over said time duration is at least 70° C. and will not burn human skin;
placing said heating element onto the surface of skin; and
simultaneously heating said heating element and operating said means for controlling said peak temperature over said time duration such that said peak temperature over said time duration is at least 70° C. and does not burn human skin.

9. The method of claim 8, wherein said peak temperature over said time duration is within a range from about 100° C.-400° C.

10. The method of claim 8, wherein said peak temperature over said time duration is about 300° C. and wherein said time duration is less than 0.1 sec.

11. The method of claim 8, wherein said means for controlling said peak temperature over said time duration comprises a control circuit and a temperature sensor, wherein said control circuit monitors said temperature sensor and prevents said heating element from heating to a temperature that would burn human skin for a given duration of time.

12. The method of claim 8, wherein said means for controlling said peak temperature over said time duration limits the total heat transferred to the skin to less than 50 J/cm$^2$.

13. The method of claim 8, wherein said means for controlling said peak temperature over said time duration limits the total heat transferred to the skin to less than 5 J/cm$^2$.

14. The method of claim 8, further comprising cooling said heating element.

15. The method of claim 8, further comprising applying a topical substance to the surface of said skin during a time selected from the group consisting of before the step of placing said heating element onto the surface of skin, during the step of placing said heating element onto the surface of skin, and after the step of placing said heating element onto the surface of skin.

16. The method of claim 8, wherein said method is used for treating a skin condition selected from the group consisting of acne, a wart and a skin wrinkle.

17. An apparatus comprising:

a housing;

a heating element attached to said housing, wherein said heating element includes a electrical insulating protective layer for placement directly onto skin;

means for heating said heating element to a peak temperature for a time duration of less than 1 second, wherein said means for heating said heating element comprises an electrical circuit configured to charge a capacitor that stores enough energy to heat said heating element; and means for controlling said peak temperature over said time duration such that said peak temperature over said time duration is at least 70° C. and will not burn human skin.

* * * * *

UNITED STATES PATENT AND TRADEMARK OFFICE
CERTIFICATE OF CORRECTION

PATENT NO. : 7,494,492 B2  Page 1 of 1
APPLICATION NO. : 11/216595
DATED : February 24, 2009
INVENTOR(S) : Luiz B. Da Silva et al.

It is certified that error appears in the above-identified patent and that said Letters Patent is hereby corrected as shown below:

Title Page, item (75)
    Inventors should read:

Inventors: Luiz B. Da Silva, Danville, CA (US); George Choi, Redwood City, CA (US); Joseph Neev, Laguna Beach, CA (US)

Signed and Sealed this

Twenty-second Day of June, 2010

David J. Kappos
*Director of the United States Patent and Trademark Office*